United States Patent [19]

Poole et al.

[11] Patent Number: 5,277,074
[45] Date of Patent: Jan. 11, 1994

[54] VARIABLE VOLUME SAMPLING CHAMBER

[75] Inventors: Trent A. Poole, South Amherst; Charles E. Lisowski, Warwick, both of Mass.

[73] Assignee: Amherst Process Instruments, Inc., Hadley, Mass.

[21] Appl. No.: 764,803

[22] Filed: Sep. 24, 1991

[51] Int. Cl.$^5$ .......................... G01N 1/24; G01N 15/02
[52] U.S. Cl. .................. 73/864.62; 73/28.01; 73/864.35; 73/863.01
[58] Field of Search ........... 73/864.62, 864.34, 864.35, 73/863.01, 863.02, 863.03, 23.33, 28.01–28.06, 865.5, 8; 31.01, 02, 03; 1G, 3

[56] References Cited

U.S. PATENT DOCUMENTS

| | | | |
|---|---|---|---|
| 3,632,210 | 1/1972 | Rich | 73/29.01 X |
| 3,854,321 | 12/1974 | Dahneke | 250/573 X |
| 3,888,109 | 6/1975 | Sharki et al. | 73/23.2 |
| 4,079,622 | 3/1978 | Cocola et al. | 73/863.12 |
| 4,151,742 | 5/1979 | Howlett et al. | 73/28.04 |
| 4,708,013 | 11/1987 | Landis | 73/23.24 |
| 4,836,039 | 6/1989 | de Silva et al. | 73/864.81 |
| 4,895,034 | 1/1990 | Poole | 73/865.5 |
| 4,917,494 | 4/1990 | Poole et al. | 356/335 |
| 4,938,592 | 7/1990 | Poole et al. | 356/335 |

Primary Examiner—Tom Noland
Attorney, Agent, or Firm—Wolf, Greenfield & Sacks

[57] ABSTRACT

Apparatus for volumetric sampling of a particle-laden gas includes a housing defining a sample chamber, a piston movable in the sample chamber so as to vary the volume of the sample chamber and a drive assembly for moving the piston in the sample chamber. The housing includes an inlet for admitting a particle laden gas into the sample chamber and an outlet for carrying the particle-laden gas from the sample chamber. The piston draws a predetermined volume of the particle-laden gas into the sample chamber through the inlet at a first flow rate during an intake phase, and exhausts the predetermined volume of the particle laden gas from the sample chamber through the outlet for analysis at a second flow rate during an exhaust phase. The outlet of the sample chamber is typically connected to a particle sizing instrument for measuring particles in the particle laden gas. The sample volume and the flow rate during the intake phase can be selected to match the parameters of the device or process being analyzed. The apparatus is useful, for example, in analyzing medication inhalers and in pollution control sampling.

28 Claims, 6 Drawing Sheets

VARIABLE VOLUME SAMPLING CHAMBER

FIELD OF THE INVENTION

This invention relates to methods and apparatus for volumetric sampling of a particle-laden gas and, more particularly, to a sampling chamber having a preselected intake flow rate and volume. The contents of the sampling chamber are exhausted to an analysis instrument at a flow rate that matches the flow rate of the instrument.

BACKGROUND OF THE INVENTION

Aerodynamic particle sizing systems are used to measure the sizes of particles in a gas. The particles can be in the form of a powder, i.e. solid particles, or droplets of a liquid. According to a time of flight measurement technique, a gas containing particles to be measured is accelerated through a nozzle and is directed through two spaced-apart laser beams in a vacuum chamber. The laser beam are detected by photomultiplier detectors. Particles passing through the laser beams cause successive output pulses on the two photomultipliers. The time required for the particles to travel between the two laser beams is a known function of particle size. The output signals from the photomultipliers are analyzed to determine particle sizes. The results of the measurement can be tabulated in a computerized system to provide a particle size distribution. The sizing system can also count the particles being measured. The total volume of particles in a sample can be determined from the number of particles and the particle size distribution. Aerodynamic particle sizing systems are disclosed in U.S. Pat. No. 3,854,321 issued Dec. 17, 1974 to Dahneke; U.S. Pat. No. 4,895,034 issued Jan. 23, 1990 to Poole; U.S. Pat. No. 4,917,494 issued Apr. 7, 1990 to Poole et al; and U.S. Pat. No. 4,938,592 issued Jul. 3, 1990 to Poole et al.

Inhalers are widely used to administer medication in the form of an aerosol to patients. A typical inhaler includes a metered dose inhalator attached to one end of a generally cylindrical chamber. The other end of the chamber is placed over the nose of the patient. When a button on the metered dose inhalator is pushed, a predetermined dose of particles of the medication is sprayed into the chamber and is inhaled by the patient.

It is important to verify the accuracy of the medication dose delivered by the inhaler to the patient. The dose depends on a variety of factors, including the inhalation characteristics of the patient, the size and type of particles that form the medication, the propellant used for expelling the medication from the metered dose inhalator, the size and shape of the chamber, etc. It has heretofore been extremely difficult to assess the performance of such inhalers under a variety of conditions. While the particle sizing systems described above accurately measure particle sizes, such systems typically have a fixed flow rate that is quite different from the flow rates at which inhalers operate. Furthermore, inhalers are designed to operate at a variety of different volumes and flow rates depending on the application. Thus, existing particle sizing systems have not been suitable for directly assessing the performance of the inhalers described above.

It is a general object of the present invention to provide methods and apparatus for volumetric sampling of a particle-laden gas.

It is another object of the present invention to provide methods and apparatus wherein a predetermined volume of a gas is drawn into a sample chamber at a first flow rate and is delivered to a measurement instrument at a second flow rate.

It is a further object of the present invention to provide methods and apparatus for measuring the dosage of particles in a predetermined volume of a particle-laden gas.

It is yet another object of the present invention to provide methods and apparatus for accurately accessing the performance of inhalers used for delivering medication in the form of an aerosol.

It is a further object of the present invention to provide methods and apparatus for volumetric pollution control sampling of smokestacks and other exhaust stacks.

SUMMARY OF THE INVENTION

According to the present invention, these and other objects and advantages are achieved in apparatus for volumetric sampling of a gas. The apparatus comprises a housing defining a sample chamber, and gas control means for drawing a predetermined volume of a gas into the sample chamber at a first flow rate during an intake phase, and for exhausting the predetermined volume of the gas from the sample chamber for analysis at a second flow rate during an exhaust phase.

The gas typically comprises a particle-laden gas, and a particle sizing system is typically connected to the sample chamber for analysis of the particle laden gas. The housing typically includes an inlet for admitting the particle-laden gas into the sample chamber and an outlet for carrying the particle-laden from the sample chamber.

The gas control means preferably comprises a piston movable in the sample chamber so as to vary the volume of the sample chamber and drive means for moving the piston in the sample chamber. The drive means preferably comprises a stepper motor, means for coupling the stepper motor to the piston and means for energizing the stepper motor during the intake phase and the exhaust phase. The coupling means preferably comprises a lead screw connected to the stepper motor and a lead screw nut connected to the piston. In a preferred embodiment, the lead screw has a relatively large pitch to provide high velocity movement of the piston.

The drive means preferably includes means for varying the first flow rate at which the particle laden gas is drawn into the sample chamber and means for varying the predetermined volume of particle laden gas that is drawn into the sample chamber. As a result, the sampling apparatus can be used for volumetric measurement of particle laden gases under a variety of conditions. For example, the sampling apparatus can be used to simulate inhalation of medication from an inhaler by a patient. The sampling apparatus can also be used for volumetric sampling of a process line.

In a preferred embodiment, a particle sizing instrument has an input port connected to the outlet of the sampling apparatus. The particle sizing instrument includes means for drawing the particle-laden gas through the input port at the second flow rate and means for measuring particles in the particle laden gas. The particle sizing instrument can also be used to determine the volume of particles in the particle laden gas.

The sample chamber typically has a cylindrical shape and the housing includes a sidewall and an end wall that define the cylindrical sample chamber. In a first embodiment of the invention, the inlet is located in the end wall, the outlet is located in the sidewall, and the housing is mounted such that the piston is horizontally movable in the sample chamber. In a second embodiment, the inlet is located in the sidewall, the outlet is located in the end wall, and the housing is mounted such that the piston is vertically movable in the sample chamber above the outlet.

According to another feature of the invention, the inlet and the outlet can be interchangeable such that the housing can be mounted for horizontal movement of the piston or for vertical movement of the piston. The configuration for vertical movement of the piston is advantageous when the particle laden gas contains relatively large particles.

According to a further feature of the invention, there is provided a method for volumetric sampling of a particle-laden gas comprising the steps of providing a housing defining a sample chamber, the housing including an inlet connected to the sample chamber and an outlet connected to the sample chamber, drawing a predetermined volume of a particle-laden gas into the sample chamber through the inlet at a first flow rate during an intake phase, and exhausting the predetermined volume of the particle laden gas from the sample chamber through the outlet for analysis at a second flow rate during an exhaust phase.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

Figure 1:
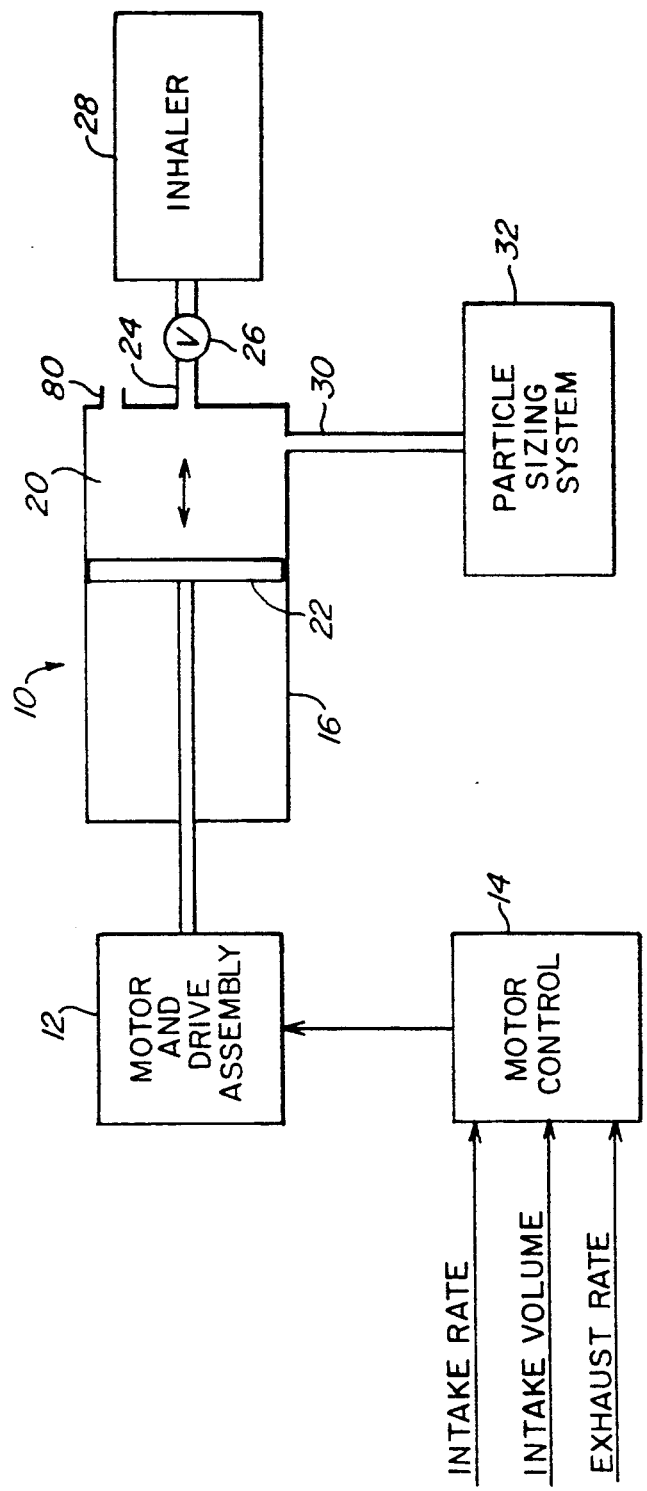
FIG. 1 is a block diagram of a measurement system incorporating volumetric sampling apparatus in accordance with the present invention.

A block diagram of a measurement system utilizing volumetric sampling apparatus in accordance with the present invention is shown in FIG. 1. The volumetric sampling apparatus of the present invention includes a sample chamber assembly 10, a motor and drive assembly 12 and a motor control 14. The sample chamber assembly 10 comprises a housing 16 that defines a sample chamber 20 and a piston 22 that is movable in sample chamber 20. The piston 22 is connected to and actuated by the motor and drive assembly 12. The housing 16 includes an inlet 24 that is connected to a source of gas to be analyzed. In the example of FIG. 1, the inlet is connected through a valve 26 to an inhaler 28. In actual practice, the valve 26 may be an integral part of the inhaler 28. The inhaler 28 typically includes a medication dispenser, or metered dose inhalator, and a chamber that is placed over the nose of the patient. The housing 16 further includes an outlet 30 connected to the input port of a particle sizing system 32. The particle sizing system can be an aerodynamic time of flight particle sizing system, such as an Aerosizer Mach II, manufactured and sold by Amherst Process Instruments, Inc. The motor control 14 controls operation of the motor and drive assembly 12, which in turn controls movement of the piston 22 in sample chamber 20.

An operating cycle of the volumetric sampling apparatus includes an intake phase and an exhaust phase. Initially, prior to the intake phase, the piston 22 is moved to the right in FIG. 1 such that the sample chamber 20 has minimum volume. The inhaler 28 to be analyzed is attached to the inlet 24, and the medication dispenser of the inhaler 28 is operated so as to spray particles of medication into the sample chamber of inhaler 28. Then the intake phase of the volumetric sampling apparatus is performed by moving the piston 22 to the left in FIG. 1, so as to increase the volume of sample chamber 20 and draw the particle-laden gas from inhaler 28 into sample chamber 20. Typically, the valve 26 is part of inhaler 28 and is a one way valve that automatically opens when piston 22 draws gas into sample chamber 20.

The velocity of piston 22 is selected to produce a desired flow rate into sample chamber 20. The flow rate is typically selected to match the rate of inhalation of a patient that would use inhaler 28. Typical intake flow rates are in the range of about 6 to 60 liters per minute. Furthermore, the travel of piston 22 is selected to draw a predetermined volume of particle laden gas into sample chamber 20. When the volumetric sampling apparatus 10 is used to evaluate inhaler 28, the volume is selected to match the volume inhaled by a patient that would use the inhaler. Typical volumes are in the range of about 1 liter or less. During the intake phase, flow through the outlet 30 is typically stopped, such as by deactivating the particle sizing system 32 or by closing a valve (not shown) at the input port of the particle sizing system 32. In some cases, the gas flow is sufficiently small that the flow during the intake phase does not adversely affect operation of the system, and flow to the particle sizing system 32 can be continued during the intake phase.

After the intake phase, a particle laden gas of known volume is contained within sample chamber 20. The exhaust phase is performed by moving piston 22 to the right so that the particle laden gas is exhausted through outlet 30 into the particle sizing system 32 for measurement of the particles. During the exhaust phase, the valve 26 is closed. The piston 22 is moved at a velocity that causes the particle-laden gas to flow through outlet 30 at the flow rate required by the particle sizing system 32. Typically, the particle sizing system 32 has a fixed flow rate on the order of about 6 liters per minute. Thus, a sample of particle laden gas of predetermined volume is drawn into sample chamber 20 at a first flow rate during the intake phase and is exhausted through outlet 30 at a second flow rate during the exhaust phase. The intake rate, the intake volume and the exhaust rate are controlled by applying suitable control signals to motor control 14 so as to control the velocity and travel of piston 22.

Figure 2A:
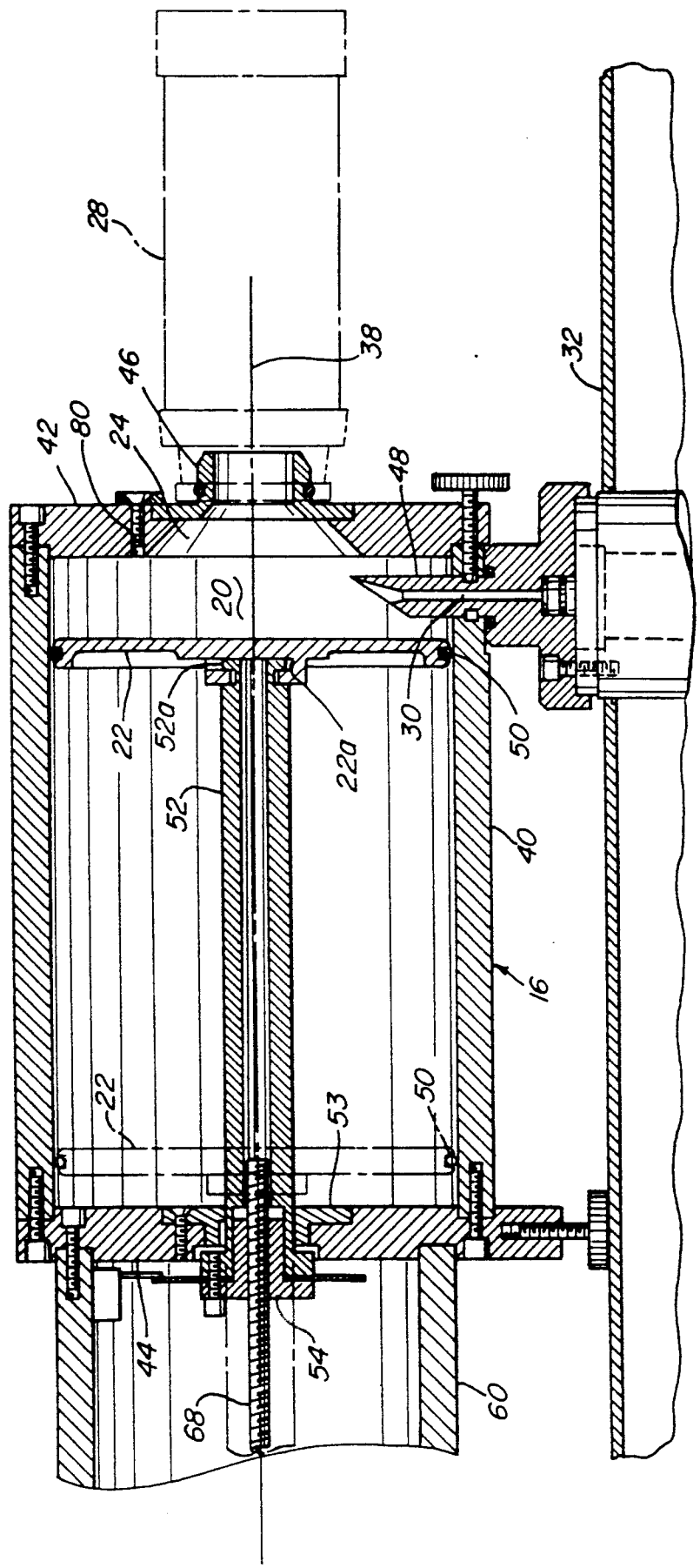
FIG. 2A is a cross section of a sample chamber and piston for a volumetric sampling apparatus in accordance with the invention.
Figure 2B:
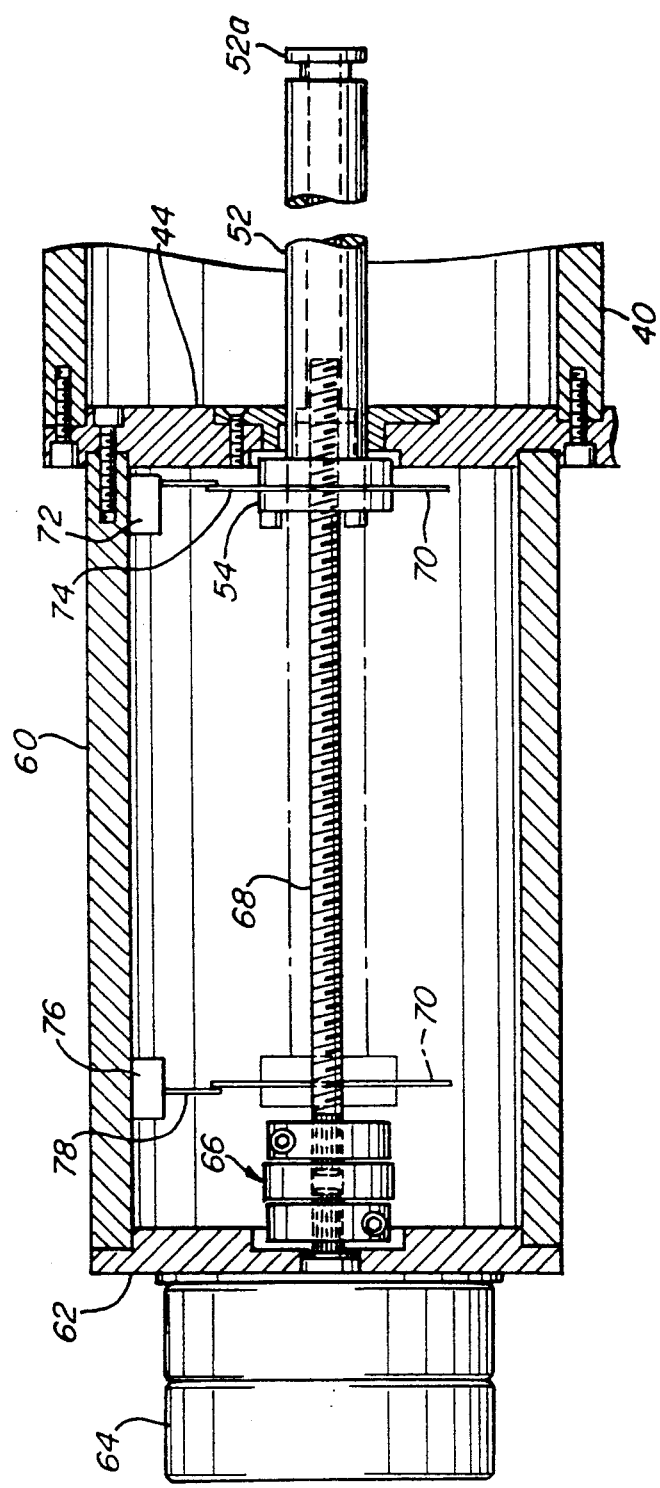
FIG. 2B is a cross section of a motor and drive assembly for the volumetric sampling apparatus of FIG. 2A.

An example of the construction of volumetric sampling apparatus in accordance with the present invention is shown in FIGS. 2A and 2B. The housing 16 defines a generally cylindrical sample chamber 20 and includes a cylindrical sidewall 40, an end wall 42 and an end wall 44. The inlet 24 is located in end wall 42 on an axis 38 of cylindrical sample chamber 20. An adapter 46 for inhaler 28 or other source of gas is mounted in inlet 24. The outlet 30 passes through the sidewall 40. An eduction tube adapter 48 for the particle sizing system 32 is mounted in outlet 30.

Piston 22 is sealed to sidewall 40 by an elastomer ring 50. The piston 22 is movable between an exhaust position, as shown in FIG. 2A, and an intake position, as shown in phantom in FIG. 2A. A piston rod 52 is attached at one end to piston 22 and extends through a piston rod bearing 53 mounted in end wall 44. A lead screw nut 54 is attached to the opposite end of piston rod 52.

The end of piston rod 52 that is attached to piston 22 is provided with a circular flange 52a. The flange 52a slidably engages a slot 22a in the center of piston 22. This arrangement permits movement of the piston 22 relative to piston rod 52 in two dimensions so that the piston 22 is self-centering in sample chamber 20. Thus, binding of piston 22 during operation is avoided.

The motor and drive assembly 12 is shown in FIG. 2B. A drive train tube 60 is mounted to end wall 44 of housing 16. A motor mount plate 62 is attached to tube 60, and a stepper motor 64 is mounted on motor mount plate 62. The shaft of stepper motor 64 extends through an opening in plate 62 and is attached by a lateral coupling 66 to a lead screw 68. The lead screw 68 extends through and engages lead screw nut 54. During operation of stepper motor 64, the lead screw 68 is rotated, thereby causing lead screw nut 54, piston rod 52 and piston 22 to move linearly in sample chamber 20. Preferably, the lead screw 68 and the lead screw nut 54 have a relatively large pitch in order to obtain a relatively high velocity of piston 22 for a given speed of stepper motor 64. The stepper motor 64 is preferably a high torque, high resolution (0.72° pole separation or better), bidirectional stepper motor. In a preferred embodiment, a Super Vexta stepper motor by Oriental Motors is used.

A striker plate 70 is affixed to piston rod 52 so as to indicate the position of piston 22. A switch 72 is mounted to a housing member such as tube 60 to sense the exhaust position of piston 22. A lever 74 of switch 72 is activated by striker plate 50 when the piston 22 reaches the exhaust position. Similarly, a switch 76 is used to sense the intake position of piston 22. The striker plate 70 activates a lever 78 of switch 76 when the piston 22 reaches the intake position. The switches 72 and 76 are used to deenergize stepper motor 64 when the piston 22 reaches either end of its travel. It will be understood that other types of position sensors, such as magnetic proximity sensors and optical sensors, can be utilized for sensing the position of piston 22 in sample chamber 20.

For operation with inhaler 28, the volumetric sampling apparatus typically has a maximum sample chamber volume of 1 liter and an intake flow rate in the range of 6 liters per minute to 60 liters per minute. These parameters provide a very close match to human breathing. The range of sample volumes and sample flow rates permits simulation of patients from typical adults to infants and special cases, such as older patients, lung impaired patients, etc. The inhaler adapter 46 preferably has an inlet diameter of about ⅜ inch to permit a relatively high flow rate into the sample chamber. The inhaler can be attached to inlet 24 with its sample chamber as described above. Alternatively, the metered dose inhalator can be connected directly to inlet 2 so that the medication is sprayed directly into sample chamber 20.

The intake flow rate, intake volume and exhaust flow rate are controlled by controlling the velocity and travel of piston 22. These parameters are determined by stepper motor 64. Techniques for controlling the pulse rate and the number of pulses supplied to the stepper motor so as to control its operation are known to those skilled in the art.

The volumetric sampling apparatus of the invention can be provided with an auxiliary inlet 80 located in end wall 42. The auxiliary inlet 80 permits the sample chamber 20 to be vented with clean gas between tests. The auxiliary inlet 80 can also be used for sampling of particle laden gas from a process line.

As indicated above, a particle laden gas drawn into sample chamber 20 can contain solid particles or liquid droplets. The particle sizes are typically in a range of about 0.1 micrometers to 200 micrometers. The configuration shown in FIGS. 2A and 2B has yielded excellent results with negligible classification or agglomeration of particles during the intake and exhaust phases, so that substantially all the particles are supplied to the particle sizing system 32.

Figure 3:
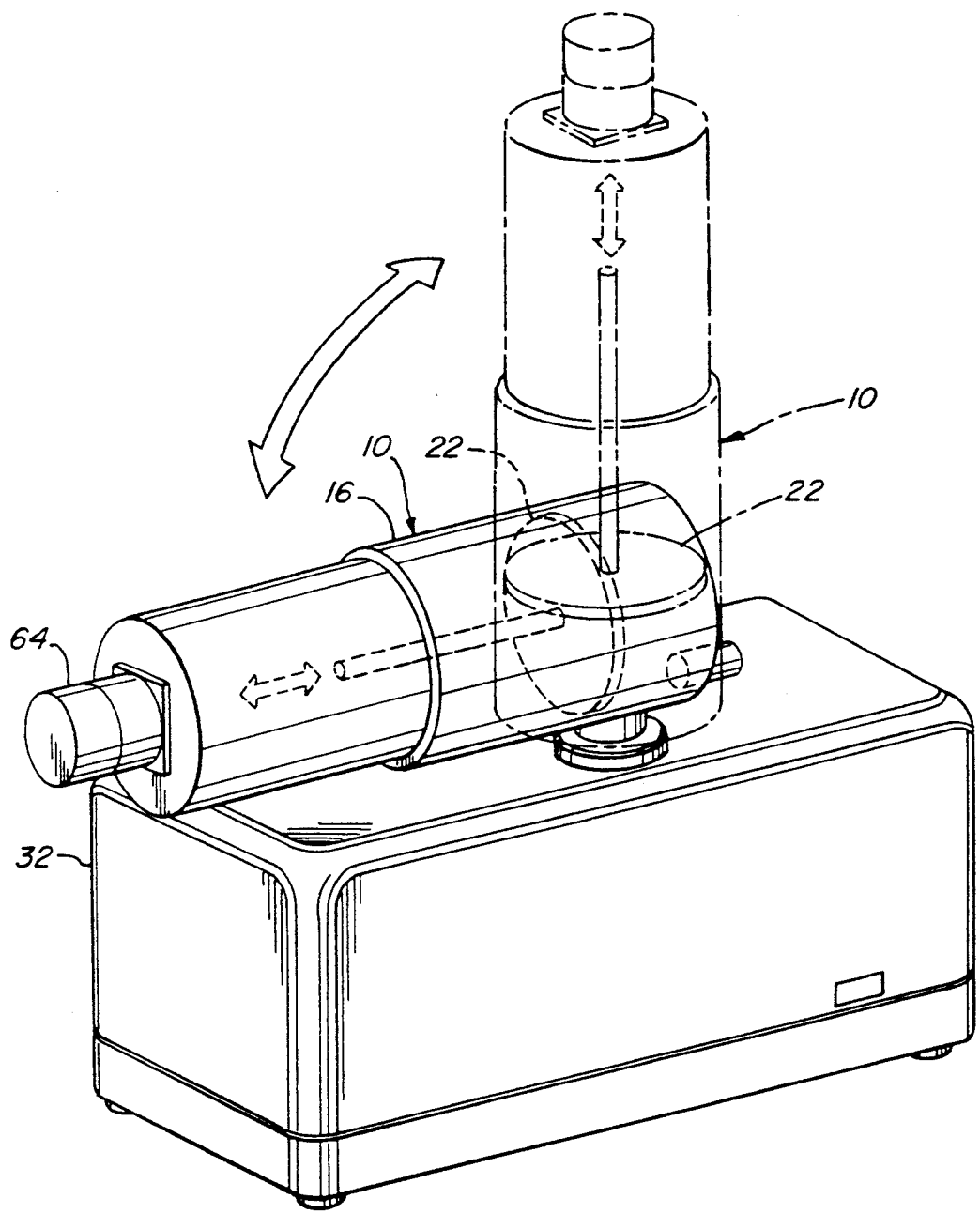
FIG. 3 illustrates volumetric sampling apparatus that is interchangeable between horizontal and vertical positions.

The volumetric sampling chamber shown in FIGS. 2A and 2B and described above is intended for horizontal operation (horizontal movement of piston 22). The mounting of a volumetric sampling apparatus on particle sizing system 32 with a horizontal orientation is shown in FIG. 3. Because the movement of piston 22 is horizontal, large particles may, in some cases, drop to the bottom of the sample chamber 20 as a result of gravity and not be exhausted to the particle sizing system 32 during the exhaust phase. In order to overcome this difficulty, a vertical orientation of the volumetric sampling apparatus can be used, as shown in phantom in FIG. 3. In this case, movement of piston 22 is vertical, and the piston 22 is located directly above the outlet of the sample chamber. Since the piston movement is toward the outlet of the sample chamber and in the same direction as the force of gravity, all particles reach the outlet to the particle sizing system 32.

The volumetric sampling apparatus can be configured for vertical operation by interchanging the locations of the inlet and the outlet of the sample chamber. For vertical operation, the outlet is located in end wall 42, and the inlet is located in sidewall 40.

Figure 4:
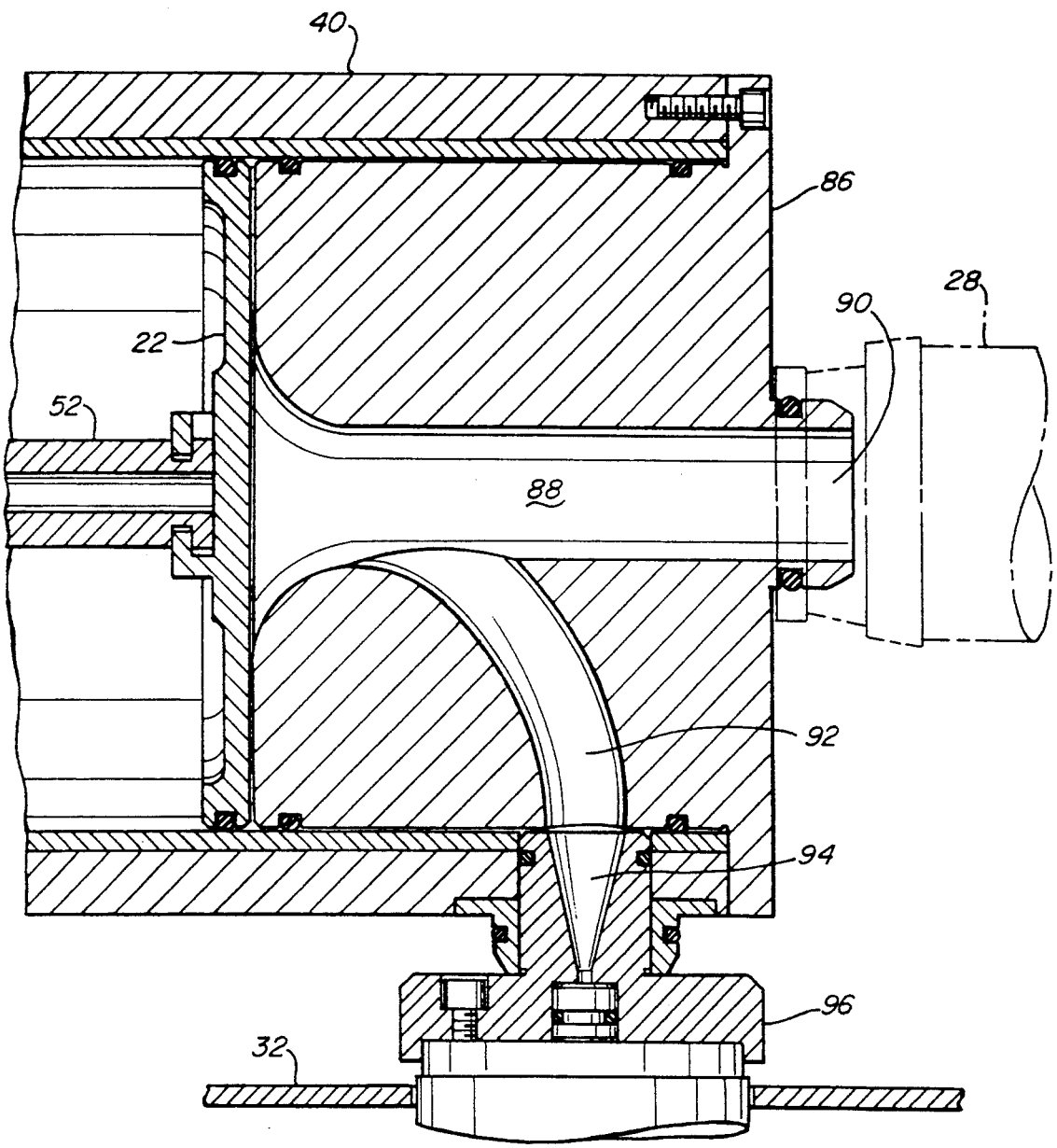
FIG. 4 is a partial cross sectional view of the interchangeable volumetric sampling apparatus, shown in a horizontal position.
Figure 5:
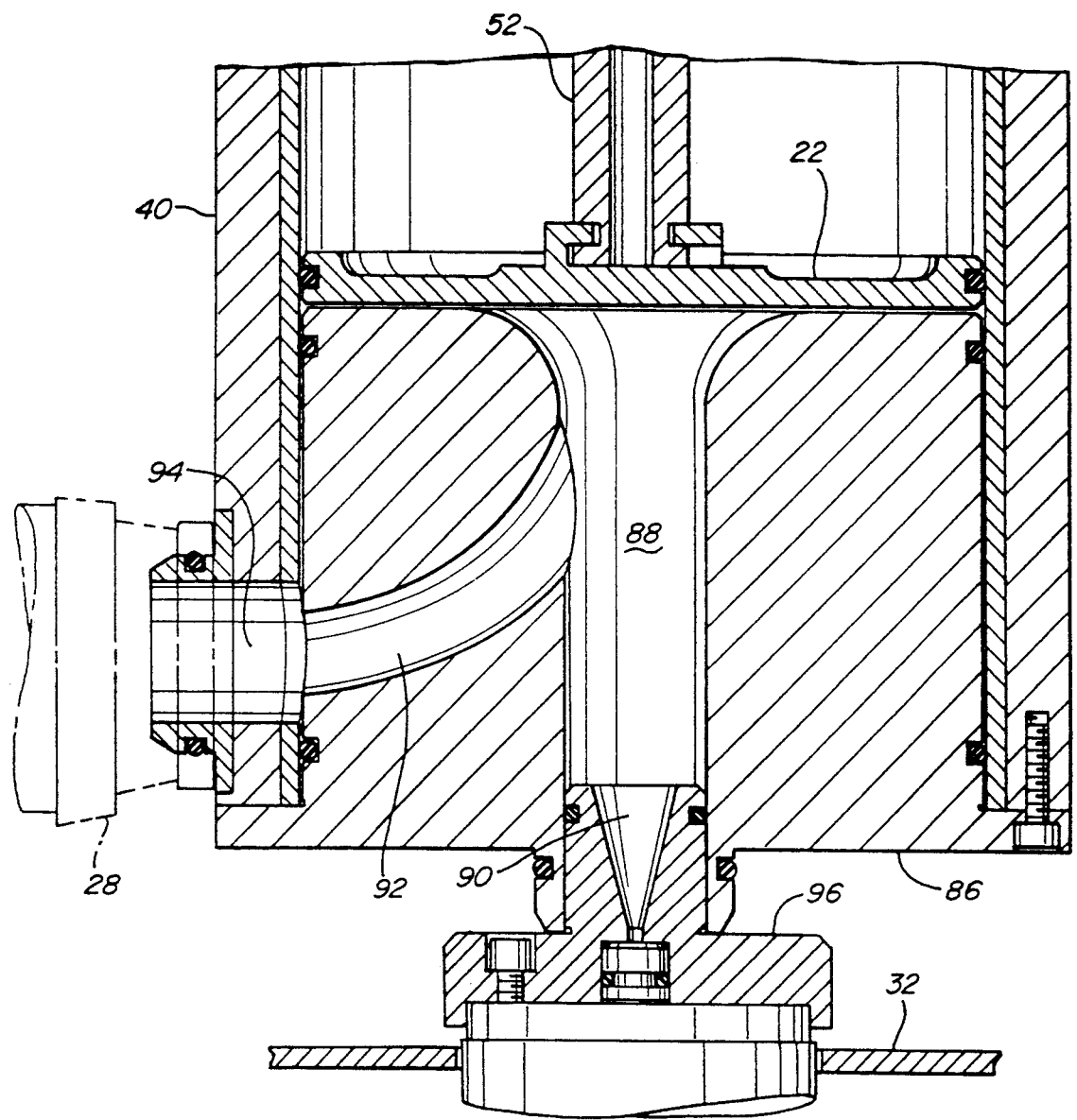
FIG. 5 is a partial cross sectional view of the interchangeable volumetric sampling apparatus, shown in a vertical position.

According to a further feature of the present invention, the volumetric sampling apparatus is configured to be interchangeable between horizontal and vertical orientations. Cross sections of an interchangeable volumetric sampling apparatus are shown in FIGS. 4 and 5. The horizontal orientation is shown in FIG. 4, and the vertical orientation is shown in FIG. 5. In the embodiment of FIGS. 4 and 5, the end wall 42 described previously is replaced with a tuned sample manifold 86. The sample manifold 86 includes an axial passage 88 connecting an axial port 90 to the sample chamber. The passage 88 is flared to a larger diameter adjacent the sample chamber. The manifold 86 also includes a curved passage 92 extending in a generally radial direction from passage 88 to a side port 94 in sidewall 40. In the horizontal orientation of FIG. 4, an inhaler is attached to axial port 90, and an adapter 96 containing an eduction tube for the particle sizing system 32 is mounted in the side port 94. In the vertical orientation of FIG. 5, the inhaler 28 is connected to side port 94, and the adapter 96 for particle sizing system 32 is mounted in axial port 90. It can be seen in FIG. 5 that particles in the sample chamber are directed by both gravity and piston 22 downwardly toward the axial port 90 and the input port of particle sizing system 32.

The volumetric sampling apparatus of the present invention has been described primarily in connection with analyzing the performance of inhalers. However, the apparatus is not limited to such use. The volumetric sampling apparatus of the present invention can be used for sampling a predetermined volume of particle-laden gas from any suitable source. The source of particle laden gas can be an intermittent source such as the inhaler or a continuous source such as a process line. The volumetric sampling apparatus of the present invention can also be used for pollution control sampling. In this application, a sample of particle laden gas is taken from a smokestack or other exhaust stack at the vent rate of the stack and is supplied to a particle sizing system as described above. For example, smokestack sampling is useful in the petrochemical industry. Furthermore, the volumetric sampling apparatus is not necessarily connected to a particle sizing system as described above. The apparatus can be used for sampling a predetermined volume of any gas, either with or without particles. For example, a predetermined volume of gas can be provided to an instrument for analysis of its composition. While examples of volumes and flow rates of the volumetric sampling apparatus have been given above, the present invention is not limited to these values.

While there have been shown and described what are at present considered the preferred embodiments of the present invention, it will be obvious to those skilled in the art that various changes and modifications may be made therein without departing from the scope of the invention as defined by the appended claims.

What is claimed is:

1. Apparatus for volumetric sampling of a particle-laden gas, comprising:
   a housing defining a sample chamber, said housing including an inlet for admitting a particle laden gas into said sample chamber and an outlet for carrying the particle laden gas from said sample chamber;
   a piston movable in said sample chamber so as to vary the volume of said sample chamber; and
   drive means for moving said piston in said sample chamber, including means for drawing a predetermined volume of the particle-laden gas into said sample chamber through said inlet at a first flow rate during an intake phase and means for exhausting the predetermined volume of the particle laden gas from said sample chamber through said outlet for analysis at a second flow rate during an exhaust phase.

2. Apparatus as defined in claim 1 wherein said drive means includes a stepper motor, means for coupling said stepper motor to said piston and means for energizing said stepper motor during said intake phase and said exhaust phase.

3. Apparatus as defined in claim 2 wherein said means for coupling comprises a lead screw connected to said stepper motor and a lead screw nut connected to said piston.

4. Apparatus as defined in claim 3 wherein said lead screw has a relatively large pitch to provide high velocity movement of said piston.

5. Apparatus as defined in claim 1 wherein said drive means includes means for varying said first flow rate at which the particle laden gas is drawn into said sample chamber.

6. Apparatus as defined in claim 5 wherein said drive means includes means for varying said predetermined volume of particle laden gas that is drawn into said sample chamber.

7. Apparatus as defined in claim 1 further including an auxiliary inlet for venting said sample chamber.

8. Apparatus as defined in claim 1 wherein said first flow rate is in a range of about 6 to 60 liters per minute.

9. Apparatus as defined in claim 1 wherein said sample chamber has a cylindrical shape and said housing includes a sidewall and an end wall of said cylindrical sample chamber, said inlet being located in said end wall and said outlet being located in said sidewall, said housing being mounted such that said piston is horizontally movable in said sample chamber.

10. Apparatus as defined in claim 1 wherein said sample chamber has a cylindrical shape and said housing includes a sidewall and an end wall of said cylindrical sample chamber, said inlet being located in said sidewall and said outlet being located in said end wall, said housing being mounted such that said piston is vertically movable in said sample chamber above said outlet.

11. Apparatus as defined in claim 1 wherein said inlet and said outlet are interchangeable such that said housing can be mounted for horizontal movement of said piston or for vertical movement of said piston.

12. Apparatus as defined in claim 1 further including sensing means for sensing limits of travel of said piston and for controlling said drive means in response to the sensed limits of travel.

13. Apparatus as defined in claim 1 further including means for sealing said piston to said housing during movement of said piston in said sample chamber.

14. Apparatus as defined in claim 1 wherein said piston is connected to said drive means by a piston rod, said piston rod having a flange that engages a slot in said piston, thereby permitting movement of said piston relative to said piston rod during movement of said piston in said sample chamber.

15. Apparatus for measuring dosage in a particle-laden gas, comprising:
   a housing defining a sample chamber, said housing including an inlet for admitting a particle-laden gas into said sample chamber and an outlet for carrying the particle-laden gas from said sample chamber;
   a piston movable in said sample chamber so as to vary the volume of said sample chamber;
   drive means for moving said piston in said sample chamber, including means for drawing a predetermined volume of the particle laden gas into said sample chamber through said inlet at a first flow rate during an intake phase and means for exhausting the predetermined volume of the particle laden gas from said sample chamber through said outlet at a second flow rate during an exhaust phase; and
   a particle sizing instrument having an input port connected to the outlet of said housing, said instrument including means for drawing said particle laden gas through said input port at said second flow rate and for measuring particles in said particle laden gas.

16. Apparatus as defined in claim 15 wherein said drive means includes a stepper motor, means for coupling said stepper motor to said piston and means for energizing said stepper motor during said intake phase and said exhaust phase.

17. Apparatus as defined in claim 16 wherein said means for coupling comprises a lead screw connected to said stepper motor and a lead screw nut connected to said piston.

18. Apparatus as defined in claim 15 wherein said drive means includes means for varying said first flow rate at which the particle laden gas is drawn into said sample chamber.

19. Apparatus as defined in claim 18 wherein said drive means includes means for varying said predetermined volume of particle-laden gas that is drawn into said sample chamber.

20. Apparatus as defined in claim 15 wherein said inlet and said outlet are interchangeable such that said housing can be mounted for horizontal movement of said piston or for vertical movement of said piston.

21. A method for volumetric sampling of a particle-laden gas comprising the steps of:
providing a housing defining a sample chamber, said housing including an inlet connected to said sample chamber and an outlet connected to said sample chamber;
drawing a predetermined volume of a particle-laden gas into said sample chamber through said inlet at a first flow rate during an intake phase by increasing the volume of said sample chamber; and
exhausting the predetermined volume of the particle-laden gas from said sample chamber through said outlet for analysis at a second flow rate during an exhaust phase by decreasing the volume of said sample chamber.

22. A method for volumetric sampling as defined in claim 21 wherein the step of drawing a predetermined volume into said sample chamber includes moving a piston so as to increase the volume of said sample chamber.

23. A method for volumetric sampling as defined in claim 22 wherein the step of exhausting the predetermined volume from the sample chamber includes moving the piston so as to decrease the volume of said sample chamber.

24. A method for volumetric sampling as defined in claim 21 wherein the step of drawing a predetermined volume into said sample chamber includes the step of selecting said first flow rate to match a rate of operation of a device under test.

25. A method for volumetric sampling as defined in claim 24 wherein the step of drawing a predetermined volume into said sample chamber further includes the step of selecting said predetermined volume to match the volume of the device under test.

26. A method for volumetric sampling as defined in claim 21 wherein the step of exhausting the predetermined volume from said sample chamber includes exhausting the predetermined volume to a particle sizing system and selecting said second flow rate to match the intake flow rate of said particle sizing system.

27. Apparatus for volumetric sampling of a gas, comprising:
a housing defining a sampling chamber; and
gas control means for drawing a predetermined volume of a gas into said sample chamber at a first flow rate during an intake phase by increasing the volume of said sample chamber, and for exhausting said predetermined volume of said gas from said sample chamber for analysis at a second flow rate during an exhaust phase by decreasing the volume of said sample chamber.

28. Apparatus as defined in claim 27 wherein said gas control means comprises a piston movable in said sample chamber so as to vary the volume of said sample chamber and drive means for moving said piston in said chamber

* * * * *